US008556860B2

(12) United States Patent
Stratton et al.

(10) Patent No.: US 8,556,860 B2
(45) Date of Patent: Oct. 15, 2013

(54) NEUROSURGICAL CAP (75) Inventors: Mathew D F Stratton, Wotton-under-Edge (GB); Hugo G Derrick, Wotton-under-Edge (GB); Max R Woolley, Wotton-under-Edge (GB)

(73) Assignee: Renishaw (Ireland) Limited, Swords (IE)

( * ) Notice: Subject to any disclaimer, the term of this patent is extended or adjusted under 35 U.S.C. 154(b) by 85 days.

(21) Appl. No.: 12/733,881

(22) PCT Filed: Oct. 8, 2008

(86) PCT No.: PCT/GB2008/003393
§ 371 (c)(1),
(2), (4) Date: Apr. 16, 2010

(87) PCT Pub. No.: WO2009/047491
PCT Pub. Date: Apr. 16, 2009

(65) Prior Publication Data
US 2010/0312193 A1 Dec. 9, 2010

(30) Foreign Application Priority Data
Oct. 8, 2007 (GB) .................................. 0719608.2

(51) Int. Cl.
*A61M 25/00* (2006.01)
(52) U.S. Cl.
USPC ........................... 604/175; 604/174; 606/129
(58) Field of Classification Search
USPC .................. 604/174, 175; 606/129
See application file for complete search history.

(56) References Cited

U.S. PATENT DOCUMENTS

| | | | |
|---|---|---|---|
| 5,800,390 A * | 9/1998 | Hayakawa et al. | 604/93.01 |
| 6,152,933 A * | 11/2000 | Werp et al. | 606/130 |
| 6,491,699 B1 | 12/2002 | Henderson et al. | |
| 2004/0034367 A1 | 2/2004 | Malinowski | |
| 2005/0027234 A1 | 2/2005 | Waggoner et al. | |
| 2005/0182420 A1* | 8/2005 | Schulte et al. | 606/130 |

FOREIGN PATENT DOCUMENTS

| | | |
|---|---|---|
| DE | 10 2006 046 346 A1 | 4/2008 |
| WO | WO 96/33766 | 10/1996 |
| WO | WO 9633766 A1 * | 10/1996 |
| WO | WO 2005/025640 A2 | 3/2005 |
| WO | WO 2009/047494 A1 | 4/2009 |

OTHER PUBLICATIONS

International Search Report issued in International Application No. PCT/GB2008/003393, on Jan. 30, 2009.
Written Opinion of the International Searching Authority issued in International Application No. PCT/GB2008/003393, on Jan. 30, 2009.
Jan. 31, 2012 Office Action issued in Chinese Patent Application No. 200880110674.X w/translation.
Nov. 26, 2012 Office Action issued in Chinese Patent Application No. 200880110674.X w/translation.
Jun. 28, 2013 Office Action issued in Chinese Patent Application No. 200880110674.X w/translation.

* cited by examiner

*Primary Examiner* — Laura Bouchelle
(74) *Attorney, Agent, or Firm* — Oliff & Berridge, PLC (57) ABSTRACT The invention relates to a cap for use in neurosurgery. The cap may be applied to a bore hole in a patient's skull, allowing the entry and removal of neurosurgical instruments, while providing an openable seal over the bore hole.

15 Claims, 6 Drawing Sheets

NEUROSURGICAL CAP

FIELD OF THE INVENTION

The present invention relates to a cap for use in neurosurgery. In particular, it relates to a sealing cap that provides a sealable channel through which one or more neurosurgical instruments can be passed.

BACKGROUND

There are many situations where there is a requirement to deliver therapeutic agents to specific targets within the brain parenchyma via implanted catheters. Furthermore, many of these therapeutic agents will cause unwanted side effects if delivered to healthy parts of the brain. Examples of treating abnormalities of brain function include the acute infusion of Gamma-aminobutyric-acid agonists into an epileptic focus or pathway to block transmission, and the chronic delivery of opiates or other analgesics to the periaqueductal grey matter or to thalamic targets for the treatment of intractable pain. Also, cytotoxic agents can be delivered directly into a brain tumour, intraparenchymal infusion can also be used to deliver therapeutic agents to brain targets that can not be delivered systemically because they will not cross the blood-brain barrier. For example, the treatment of patients with Parkinson's disease, Alzheimer's disease, head injury, stroke and multiple sclerosis maybe carried out by the infusion of neurotrophic factors to protect and repair failing or damaged nerve cells. Neurotrophins may also be infused to support neural grafts transplanted into damaged or malfunctioning areas of the brain in order to restore function. It is also known to insert instruments other than catheters, such as electrodes, directly in the brain parenchyma. For example, stimulating and lesioning electrodes are used in a variety of surgical procedures, including deep brain stimulation (DBS) electrodes. A surgeon wishing to stimulate or lesion a particular area of nervous tissue can target the end of an electrode to the target site so that a desired electrical current can be delivered.

Once a catheter or electrode has been inserted into the target area, it may need to remain in place for some time. It would be useful to be able to substantially seal the channel through which the instrument has been passed, so as to reduce the likelihood of the ingress of micro-organisms etc. it would also be advantageous to be able to remove the instrument without opening the seal. In addition, it is often necessary to administer a course of treatment to the same area repeatedly and so a surgeon may need to access the patient's brain through the same channel on a number of occasions. It would be helpful to be able to do this, without repeated opening of the channel surgically.

SUMMARY OF THE INVENTION

According to a first aspect of the present invention, there is provided a cap for closing a communication channel in a patient's skull. The cap comprises a body that is attachable to the skull of a subject over a preformed hole in the skull, the body defining a channel through which one or more neurosurgical instruments can be passed, and an openable seal for sealing the channel.

The present invention thus provides a cap that can be located within or over an aperture or hole formed in the skull of a subject. The cap comprises an openable sealed access channel or passageway, through which a neurosurgical instrument, such as a tube or a wire, can be passed, allowing communication between the outer surface of a patient's skull and the patient's brain cavity.

The body of the cap preferably comprises means for allowing the body to be attached to the patient's skull. In particular, such means are likely to be one or more, preferably at least two, more preferably three or four holes through which a screw may be passed and screwed into the patient's skull, thereby anchoring the body to the skull.

The body may be of any appropriate shape to allow attachment to the patient's skull and to define at least one channel. The channel defined by the body may be selected in size and shape to correspond to a hole drilled in a patient's skull. The channel is preferably circular. The channel may be any size, but is preferably less than 8 mm in diameter, more preferably less than 6 mm in diameter.

The cap comprises at least one sealing element to seal the passageway or channel into the patient's brain. A variety of sealing elements may be used. Preferably, the sealing element is a septum seal or similar seal that defines at least one channel through which a neurosurgical device can be passed, the channel being self sealing, that is to say will close substantially when the device is removed. The septum seal may take the form of a membrane or a bung, for example. The septum seal may also define more than one channel through which a neurosurgical instrument may be passed.

As indicated above, a number of shapes of body are envisaged. In a preferred embodiment, the body sits on the surface of the patient's skull. In that embodiment, the body has a lower contact surface that is preferably arranged to sit on the surface of the patient's head, an upper surface and a side wall. The lower contact surface may be substantially flat. The diameter of the body is larger than the hole in the patient's skull and the surface wall is shallow, being approximately 1 to 5 mm in height. The body may be any shape, but is preferably generally annular.

With a body of this nature, a number of septum seals may be used. The seal may be a flat, membrane like seal that extends across the body channel. Alternatively, the seal may be a deeper, bung like seal that not only seals the body channel, but also extends into the hole made in the patient's skull. Such a seal may be cylindrical or have the shape of an inverted cone.

When the septum seal extends into the hole provided in the patient's skull, the cap may also comprise a seal housing, which is arranged to extend into the hole in the patient's skull and to be located between the seal and the patient's skull bone.

Alternatively, part of the body may be arranged to be located within the hole made in the patient's skull, thereby providing an integrally formed housing for the septum seal. In that second embodiment, the body is preferably cylindrical in shape and has a substantially annular shoulder, the cylindrical body extending into the hole in the skull and the shoulder sitting on the surface of the patient's head. The means for allowing attachment of the body are preferably found on the annular shoulder.

The body of the skull mount may be made from a material that is appropriate to remain in situ for an extended period of time. Preferably the material chosen is reasonably rigid, so as to avoid the body changing shape or deforming substantially if a force is applied. However, in order to allow a skull mount according to the invention to be attached to a patient's skull at any one of a number of different locations on the patient's head, it is important that the body of the skull mount has some flexibility. This allows the body to conform to the shape of the patient's skull. This flexibility may be provided by weakening areas of the body in the region of the means for allowing attachment. For example, a number of lines of weakness may be formed on the annular body or on the annular shoulder of the cylindrical body. The body is able to flex along these lines of weakness, so that it will conform to the shape of the patient's head.

To aid positioning and removal of an instrument used with the cap, the cap is preferably provided with at least one instrument exit point. Preferably, the body has a plurality of exit points to allow either a plurality of instruments, especially catheters to be used simultaneously or to the position of one instrument to be selected from a number of options. The exit points may be formed in the body, in the seal, or both. Each exit point may comprise a channel, passageway, trench or a groove in the body or seal, through which the instrument may be passed. Further, each exit point may be provided with a locking means to hold an instrument in place once inserted. For example, where the exit point is a groove or recess, the exit point may be sized such that the instrument fits snugly within the groove or recess. Part of the groove or recess may be locally narrowed, so that the instrument can still be inserted into the narrowed part, but once inserted is held in place. The exit point allows the instrument to be removed from the patient, by a surgeon or suitably trained clinician, simply pulling the instrument out, whilst preventing the end of the instrument from straying significantly from its inserted trajectory.

To further assist in sealing the hole in the patient's skull, the cap may also comprise a cap seal. The cap seal is arranged to be positioned over the septum seal when the instrument has been inserted. The cap seal provides further sealing around the area of insertion of the instrument. The cap seal and septum seal are preferably shaped to fit together snugly. The cap seal may comprise an instrument guide, such as a channel or groove, through which the instrument can pass, again to improve the fit between the cap and septum seal. Additionally the instrument guide may coordinate with the instrument exit point.

The septum seal is preferably made, at least partially, of a soft elastomer to allow the seal to deform slightly when the instrument is introduced. The cap seal may also be made of a soft elastomer, allowing it to deform around the instrument and maintain a close seal.

Further, the cap may be provided with a cap top which fits over the cap body. When a cap top is used, the body may have an annular groove around side wall of the body or of the shoulder. The cap top fits on to the body and the sides of the top preferably snap fit into the annular groove. To aid this snap fit, the underside of the cap top may be shaped to fit into the groove. For example, the cap top may comprise an O ring near to the edge of the underside of the cap top. In addition, the edge of the cap may be provided with a deformable skirt which fits closely with the patient's head but deforms to allow an instrument to exit from the cap body under the skirt. On the underside of the cap, a second O ring may also be provided. The second O ring fits on top of the cap seal, holding the cap seal in place and providing further sealing. Alternatively, the cap may be used without a cap top. In that case, in use, the body may be covered with bone wax.

In an alternative embodiment, the cap seal may be temporarily replaced by a septum guide.

As noted above, the cap is advantageously suitable for long term, percutaneous, implantation within a subject. Long term implantation may mean the skull mount remaining with the body for weeks, months or even years at a time; i.e. long after the initial surgical intervention. In such a case, the cap is conveniently formed from materials that are suitable for long term implantation within the body. For example, the cap body may be formed from titanium or a plastic material such as Barex (Trademark), PEEK (Polyaryletheretherketone) or a thermoplastic polyurethane elastomer (TPU) such as Carbothane (Trademark). The cap is conveniently fabricated from a material that is opaque to x-rays or is detectable using MRI so that it can be readily identified after implantation. Conveniently, the cap comprises only non-magnetic material so that a patient with the cap implanted therein can be safely subjected to an MRI scan. As outlined in more detail below, the implanted cap maybe provided as part of a long term implanted drug delivery or deep brain stimulation system.

Also provided by the invention is a method for inserting a neurosurgical instrument comprising the steps of (i) attaching the body from a cap according to the invention to the patient's skull, over a hole in the patient's skull, the body of the cap being sealed by a body seal; (ii) passing an instrument through the body seal; and (iii) placing the instrument into the exit point in the cap body.

The method may also include one or both of the steps of (iv) placing a cap seal onto the cap; and (v) placing a cap top onto the cap.

The cap of the invention may be used with a guide or skull mount, such as that described in UK Patent Application No. 0723880.1 and applications claiming priority therefrom.

DETAILED DESCRIPTION OF THE INVENTION

The cap according to the invention will now be described in detail, by way of example only, with reference to the drawings in which:

FIGS. 1 to 4 show a first embodiment of the cap.

In a first embodiment, as shown in FIGS. 1 to 4, the cap 10 comprises a body 12, that is generally annular in shape. The body defines a channel, 14, through which surgical instruments may be passed. Extending from the annular body are three arms, each having an aperture 16 through which a bone screw may be passed to attach the body to a patient's skull. In order to allow the body to conform to the shape of the surface of the patient's skull, the body is provided with flexion regions, 17 which are lines of weakness, along which the body can flex.

The cap body is used with a seal housing 18. The seal housing is cylindrical, and is provided with a lip 20. The housing fits into the hole in the patient's skull, beneath the cap body, the lip resting on the surface of the patient's head. A body seal 22, fits inside the housing, sealing the channel in the body. The body seal itself has a preformed channel through which an instrument can be passed. The body seal is formed from an elastomeric material that may be deformed by the instrument to allow insertion.

The body and the body seal cooperate to provide a path for the inserted instrument. The seal and upper surface of the body are curved 24, to provide a smooth path for the instrument. Also, the body is provided with three instrument exit points 26, through which the inserted instrument can exit the cap. Corresponding exit guides 28 are provided on the body seal. In this embodiment, the exit points are channels in the cap body.

The cap further comprises a cap seal 30 shaped to fit into the top of the body seal.

Finally, there is a cap top 32 which fits over the other components of the cap. The cap top snap fits onto the cap body, the edge 34 of the body snapping into a groove 36 in the wall of the body. The edge of the cap top is provided with openings to allow easy exit of the instrument.

Figure 1:
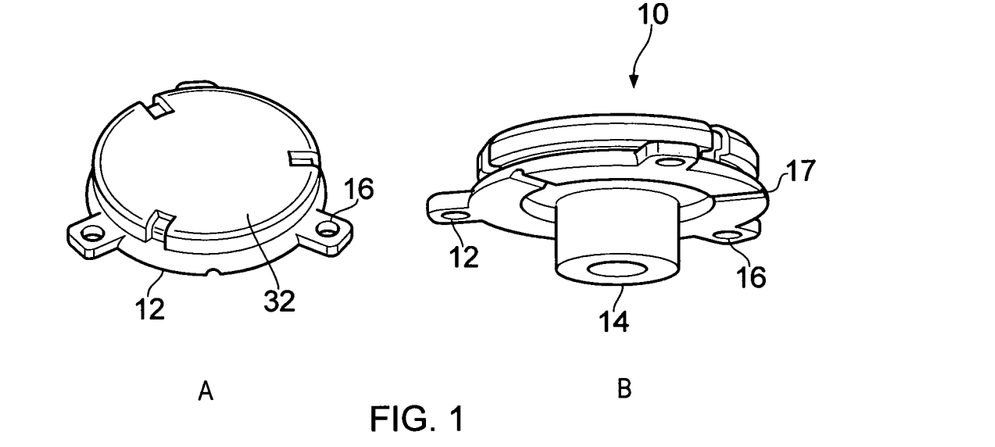
FIG. 1 showing a top view assembly (A) and a bottom view assembly (B), FIG. 2 showing an exploded top view of the component parts, FIG. 3 showing a section of the assembly, FIG. 4 showing a bottom exploded view of the component parts.
Figure 2:
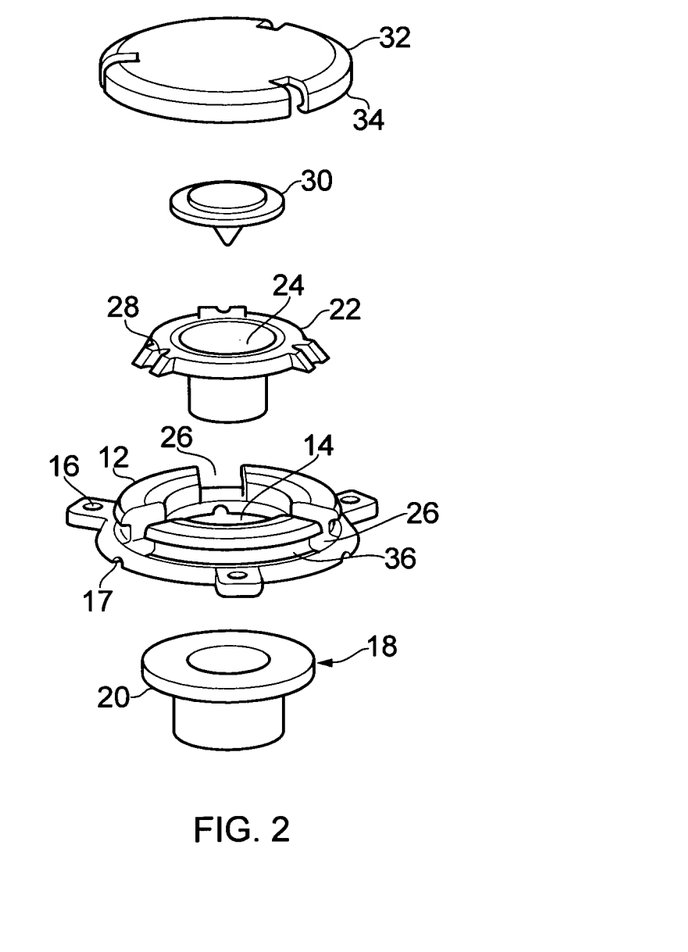
Figure 3:
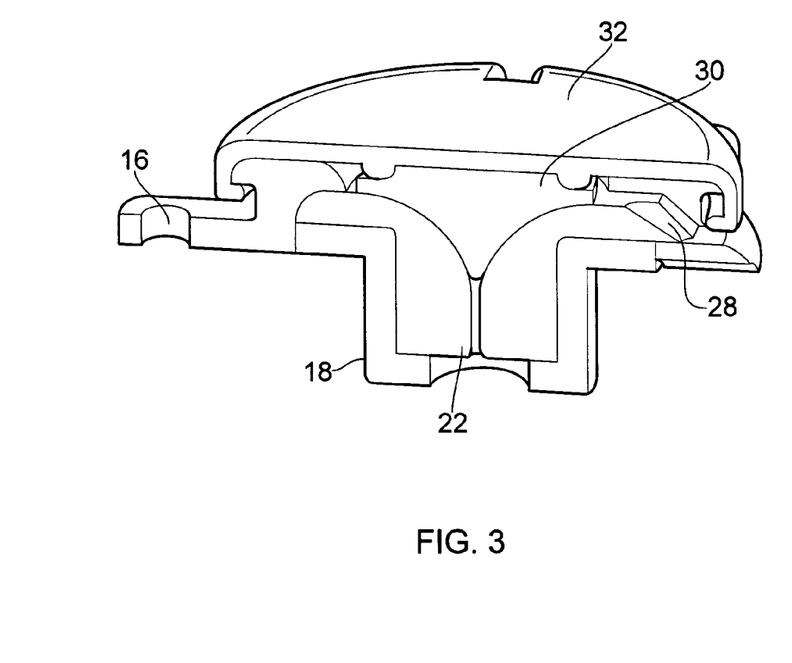
Figure 4:
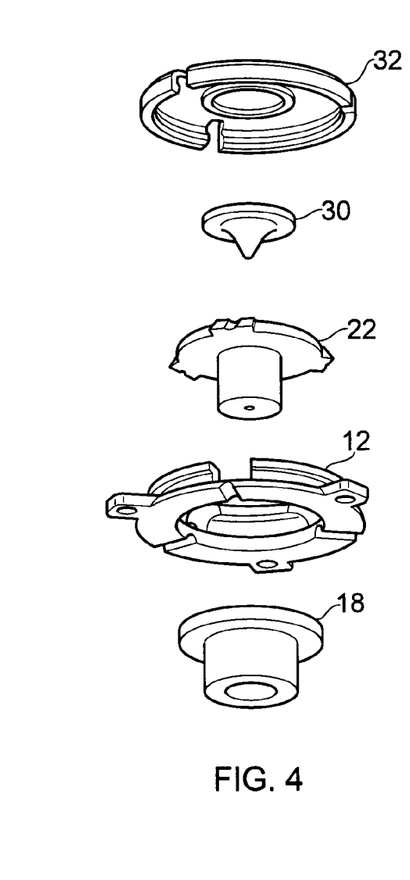

FIG. 3 shows the assembled cap. The housing 18 is inserted into the hole in the patient's skull and the body seal placed inside the housing. The body is placed over the housing and screwed into place. The instrument, such as a catheter, is inserted through the instrument path in the body seal and follows the curved surface of the body seal. This prevents kinking of the instrument and minimises stress during implantation or removal. The instrument exits the cap via the exit guide and exit point. The cap seal is then placed on top of the body seal. The cap seal and body seal are made of an elastomeric material and deform around the instrument, improving the seal. The cap top is then placed on top of the body. The edge of the cap top snaps into the groove around the wall of the body.

When wishing to remove the instrument, a surgeon or other medical practitioner does not need to remove the cap top or cap seal. The surgeon can simply pull the instrument from the cap. To aid a steady removal, the surgeon can apply pressure to the cap top. The curved surface of the body seal, combined with the exit guide and exit points provides a smooth path through which the instrument passes. As it is removed, the instrument remains on its inserted trajectory, so as not to cause damage to the brain tissue.

Figure 5:
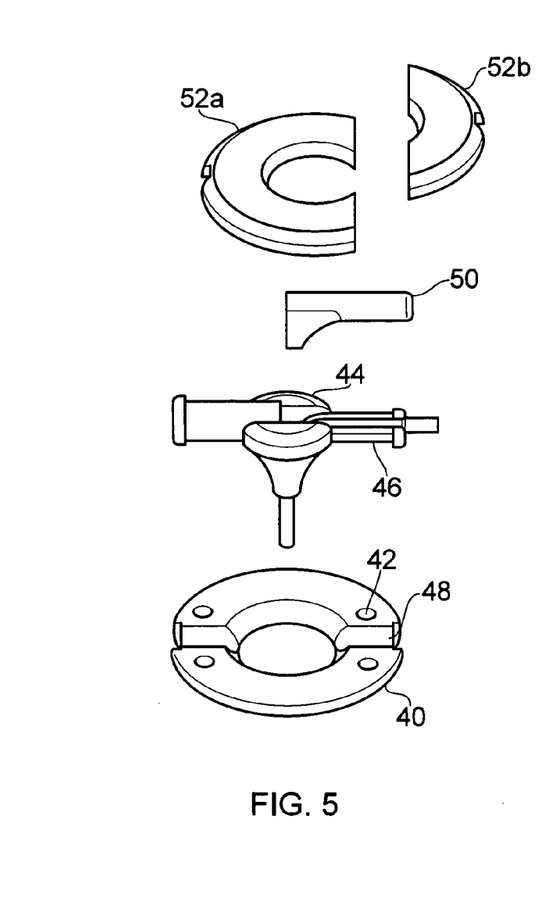
FIG. 5 shows an exploded view of a second embodiment of the cap.
Figure 6:
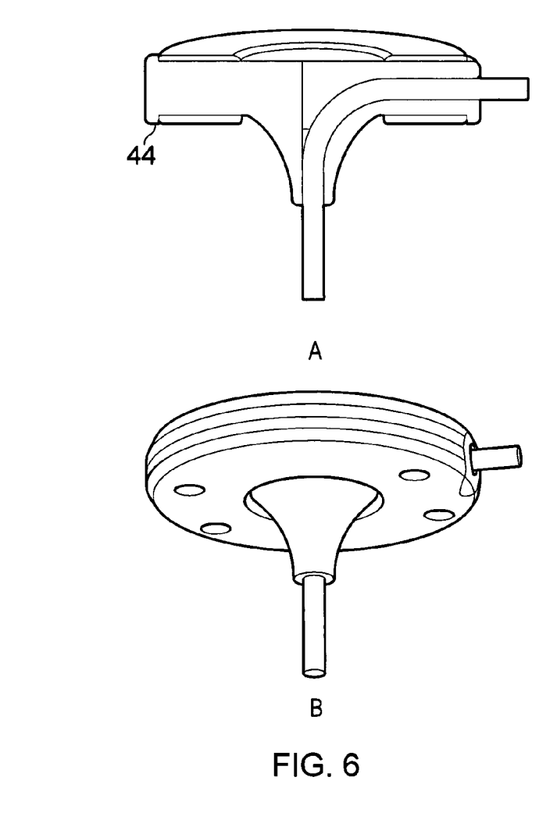
FIG. 6 shows a bottom view of the second embodiment (A) and a section of the second embodiment (B)

In a second embodiment, as shown in FIGS. 5 and 6, the cap comprises four components, an annular body 40 defining a channel which can be attached to the patient's skull using screws that fit through apertures 42 in the body. The cap also comprises a body seal 44, which fits through the body channel into the patient's brain cavity. The body seal defines an instrument channel having a curved path, through which an instrument may be passed. The curved path of the instrument channel has a large radius, allowing for a wide range of instrument trajectories. The body seal may take the form of a duck seal or a polyp seal which may be self sealing on the removal of the instrument. Alternatively, the seal can be manually activated via the scalp or cap top. The instrument exits the seal via an exit guide 46 which fits into a corresponding exit point 48 in the cap body. To maintain the position of the instrument in the exit guide, the cap also comprises a cap seal 50, which fits into the body seal, over the instrument. The cap top 52 is fitted over the body and seals to hold the components in place. The edge of the cap top snaps into a groove in the edge of the body. The cap top may comprise two separate parts, a main part 52a, which can remain on the cap whilst the instrument is inserted, and a secondary part, 52b, which may be removed to insert the instrument. The cap top in this embodiment is annular and has a central aperture. This aperture can be filled by a further cap top portion or seal to provide additional sealing, if required.

Figure 7:
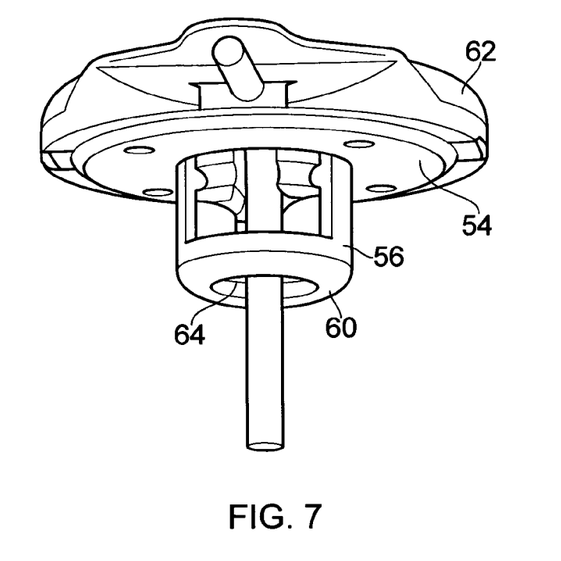
FIG. 7 shows a partial section of a third embodiment.
Figure 8:
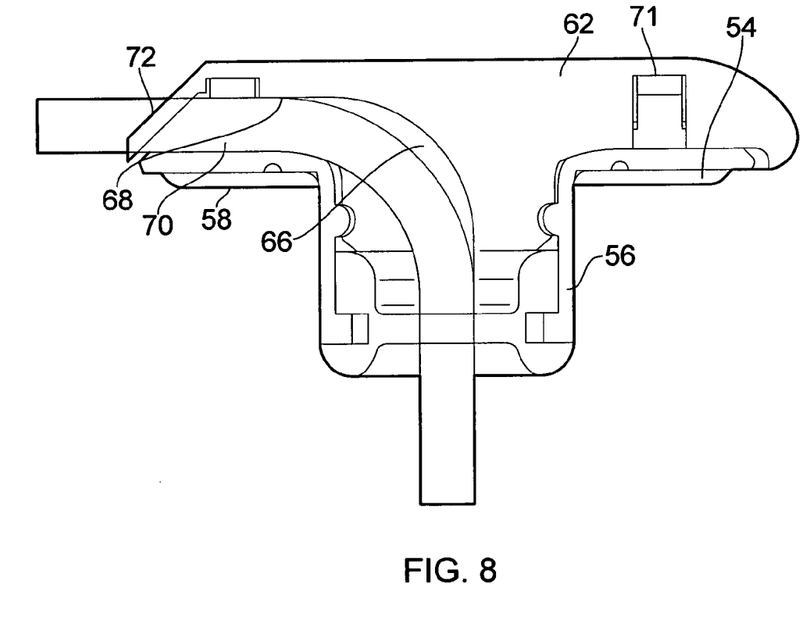
FIG. 8 shows a section of a fourth embodiment.

In third and fourth embodiments, as shown in FIGS. 7 and 8, the cap body 54 has a cylindrical portion or boss 56, from which an annular shoulder 58 extends. The cylindrical portion fits into a hole in the patient's skull. The body can be attached to the skull using screws inserted through apertures in the shoulder. Slots in the underside of the annular portion allow the annular portion to conform to the patient's skull shape. A body seal 60 is found in the lower end of the cylindrical portion. The body and body seal are provided with a corresponding groove and ridge which fit together to hold the body seal in place. The cap further comprises an integrated cap seal and cap top 62 which fits into the cylindrical portion above the body seal. Again, the cap seal and body may be provided with a corresponding lip and groove to hold the cap seal in place. The body seal, cap seal and body combine to provide a passageway through which an instrument can be inserted. A substantially straight channel 64 is provided in the body seal. The cap seal comprises a curved channel 66 and, in its upper region, comprises an exit guide 68 which combines with an exit point 70 in the body to form the passageway. The passageway is curved and has large controlled radii, which prevents kinking of the instrument and aids removal. The exit point 70 on the body is made up of a groove in the body. In the fourth embodiment, the exit point also include a hook 71 or lip which clips over the instrument to aid positioning, hold the instrument in place and aid removal. The edge of the cap top comprises a flap 72 which seals the exit point after the instrument is removed. The third and fourth embodiments may also include a mesh reinforcement plug 74 between the body seal and cap seal. The plug may be made, for example, from cellulose. It provides additional support for the instrument and can act as a saline reservoir to prevent infection and to aid lubrication on removal of the instrument.

Figure 9:
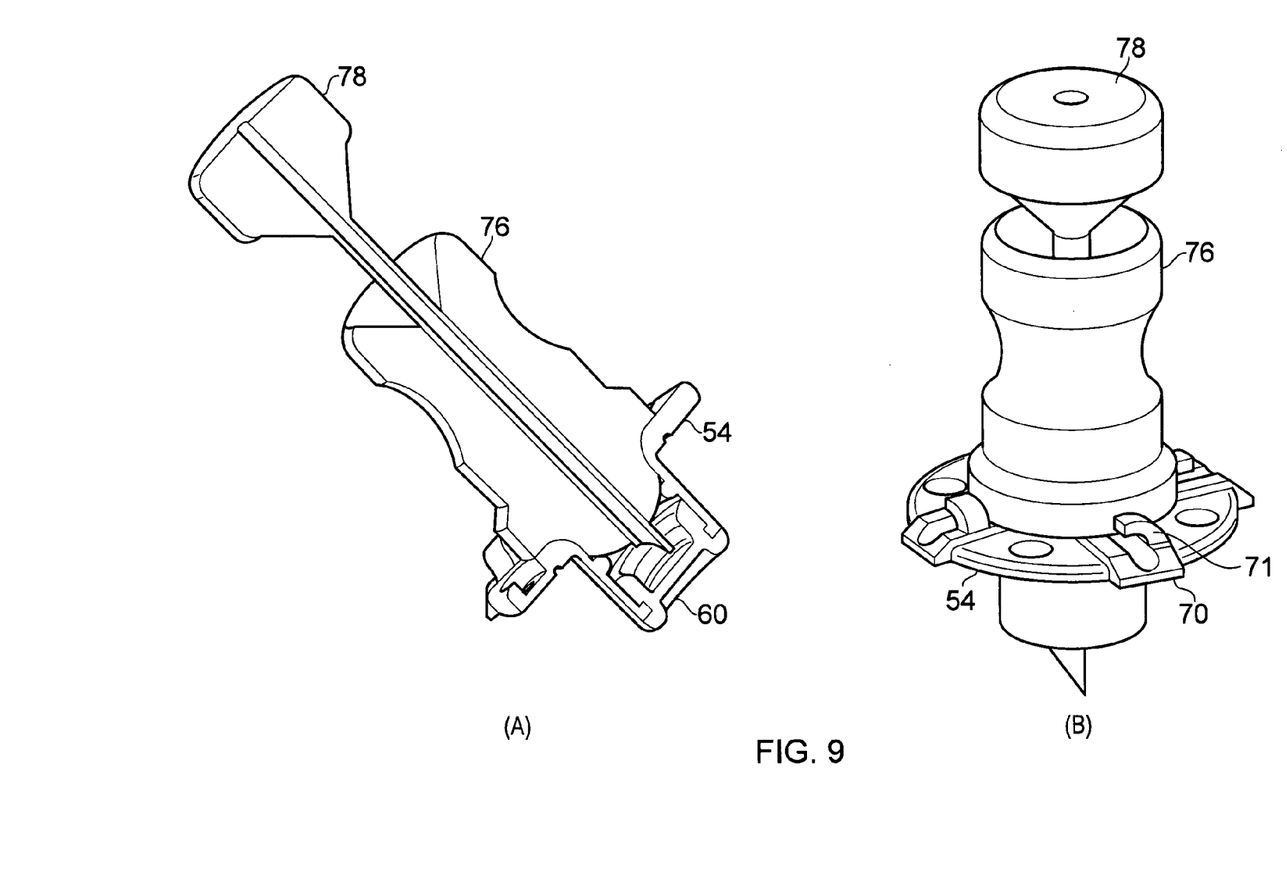
FIG. 9 shows a sectioned view (A) and a top view (B) of a fifth embodiment including a septum guide.

In the fifth embodiment, the body and body seal are similarly arranged to the third and fourth embodiments. This embodiment can also be used with a cap top or cap seal. As an alternative; however, the cap seal may be replaced with a septum guide 76 and a piercing cannula 78, as shown in FIG. 9. The septum guide comprises an elongate guide component that fits into the cap body. A piercing cannula can be passed through a central hole in the septum guide and through the septum and dura of the patient's brain. The cannula may then be removed and a desired instrument inserted. Use of the piercing cannula helps to prevent deflection from the trajectory angle. The caps described herein may usually be used for a range of trajectory angles, that is with insertion trajectories that are not parallel to the cap trajectory. The septum guide may be pivoted within the body in order to set the trajectory angle. The septum guide may then be held in place by an external clamp. Alternatively, when the insertion trajectory is parallel to the cap trajectory, the septum guide may be locked into the cap body, the septum guide being provided with a ridge or groove which locks with a corresponding groove or ridge on the cap body.

Figure 10:
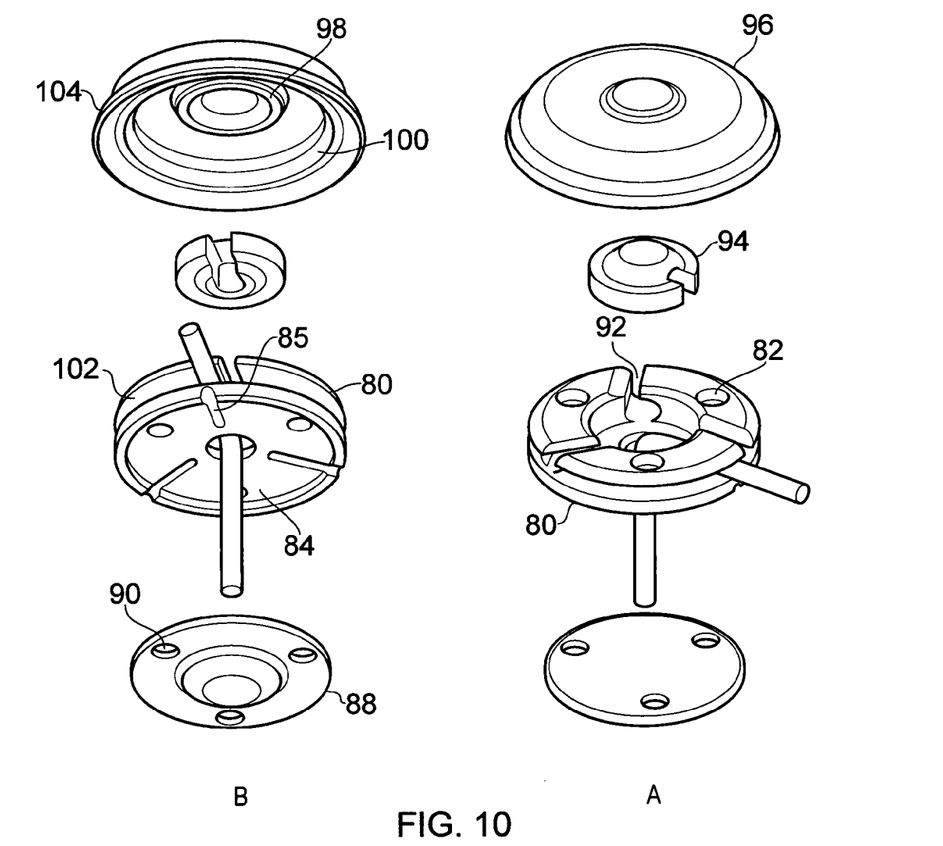
FIG. 10 shows top (A) and bottom (B) exploded views of the components of a sixth embodiment.

A sixth embodiment is shown in FIG. 10. The embodiment comprises an annular body 80 having three holes 82 through which screws may be inserted to attach the body to the patient's skull. The body defines a channel 84, through which an instrument may be passed. The edge of the channel is rounded, to provide a smooth passage for the instrument. The body comprises flexion regions 85 weakened regions along which the body may flex to allow the body to conform to the shape of the patient's skull. The cap also comprises a septum seal 88, which also comprises holes 90 through which the skull screws pass, fixing both the seal and the body to the skull. In use, the instrument is passed through the channel and septum seal. The instrument is then bent over and placed into the exit point 92, a slot in the body. The instrument may be locked in place as the slot is narrowed so that the instrument fits snugly within it. The instrument may be removed by pulling it through the slot. To aid in the safe removal of the catheter, the embodiment further comprises an instrument guide which fits on top of the seal. The instrument guide comprises an exit guide 94 which fits over the instrument and directs it into the exit point. The instrument guide protects the instrument from being crushed by load applied to the cap. The cap also comprises a cap top 96. The cap top comprises a central O ring 98 that fits onto the instrument guide and holds it in place, and a peripheral O 100 ring which fits into a groove 102 around the side wall of the body and provides additional sealing. At the periphery of the cap, there is a deformable skirt 104 which moulds around the exiting instrument and which returns to its original position once the instrument has been removed to maintain sealing.

The use of the sixth embodiment will now be described. It will be appreciated that the use of the other embodiments will follow a similar work flow. The site for a burr hole is localised on the skull. A burr hole of approximately 8 mm is drilled in the skull. The dura depth is determined and a guiding device aligned (for example, stereotactically). The depth of the target is determined and the cap aligned with the burr hole, an aperture created in the dura, and the device placed and screwed into position. A catheter or other instrument is selected and the target depth marked on the catheter. The catheter is then implanted using the guiding device. Following implantation, the guiding device is removed and the catheter folded and positioned in the exit point slot. The instrument guide (or cap seal) is then placed over the catheter. The cap top is then placed over the cap, a tunnel created and the catheter externalised.

Whilst a variety of features have been described in the different embodiments, it should be appreciated that features from different embodiments can be combined.

The invention claimed is:

1. A neurosurgical cap comprising:
   a body that is attachable to a skull of a patient, the body defining a channel configured to pass one or more neurosurgical instruments into a brain; and
   an openable seal for sealing the channel, wherein
   the seal is a septum seal configured to allow the one or more neurosurgical instruments to be passed through said channel and to sealably engage the one or more neurosurgical instruments, and
   the cap allows an implanted device to be explanted by pulling on the device, without having to surgically open the patient's scalp.

2. The cap according to claim 1, further comprising means for allowing the body to be attached to the patient's skull.

3. The cap according to claim 1, wherein the body is substantially annular.

4. The cap according to claim 1, further comprising a skull penetrating portion and an annular shoulder for fixing the body to the skull.

5. The cap according to claim 1, further comprising a seal housing.

6. The cap according to claim 1, wherein the body comprises at least one instrument exit point.

7. The cap according to claim 1, further comprising an instrument guide.

8. The cap according to claim 7, wherein the instrument guide comprises an exit guide.

9. The cap according to claim 1, further comprising a cap top.

10. A neurosurgical kit comprising the cap according to claim 1 and a septum guide.

11. A neurosurgical cap comprising:
    a body that is attachable to a skull of a patient, the body defining a channel configured to pass one or more neurosurgical instruments into a brain; and
    an openable seal for sealing the channel, wherein
    the seal is a septum seal configured to allow the one or more neurosurgical instruments to be passed through said channel and to sealably engage the one or more neurosurgical instruments, and
    the body comprises at least one weakened region, in which the body can flex.

12. A neurosurgical cap comprising:
    a body that is attachable to a skull of a patient, the body defining a channel configured to pass one or more neurosurgical instruments into a brain;
    an openable seal for sealing the channel, wherein the seal is a septum seal configured to allow the one or more neurosurgical instruments to be passed through said channel and to sealably engage the one or more neurosurgical instruments; and
    a cap seal.

13. The cap according to claim 12, wherein the cap seal comprises an exit guide.

14. A neurosurgical cap comprising:
    a body that is attachable to a skull of a patient, the body defining a channel configured to pass one or more neurosurgical instruments into a brain;
    an openable seal for sealing the channel; and
    a cap top, wherein
    the seal is a septum seal configured to allow the one or more neurosurgical instruments to be passed through said channel and to sealably engage the one or more neurosurgical instruments, and
    the cap top comprises at least one O ring.

15. A neurosurgical cap comprising:
    a body that is attachable to a skull of a patient, the body defining a channel configured to pass one or more neurosurgical instruments into a brain;
    an openable seal for sealing the channel; and
    a cap top, wherein
    the seal is a septum seal configured to allow the one or more neurosurgical instruments to be passed through said channel and to sealably engage the one or more neurosurgical instruments, and
    there is a groove in the side wall of the body.

* * * * *